United States Patent [19]

Haq

[11] Patent Number: 4,473,611

[45] Date of Patent: Sep. 25, 1984

[54] POROUS POLYMERIC MATERIAL CONTAINING A REINFORCING AND HEAT-SEALABLE MATERIAL

[75] Inventor: Zia Haq, Wirral, England

[73] Assignee: Lever Brothers Company, New York, N.Y.

[21] Appl. No.: 553,620

[22] Filed: Nov. 21, 1983

[30] Foreign Application Priority Data

Nov. 26, 1982 [GB] United Kingdom ............... 8233751

[51] Int. Cl.$^3$ ..................... A47L 13/16; A47L 17/00; B32B 3/00; B32B 5/22

[52] U.S. Cl. .................................. 428/198; 428/200; 428/211; 428/246; 428/283; 428/286; 428/287; 428/316.6; 428/913; 15/118

[58] Field of Search ............... 428/195, 198, 200, 211, 428/246, 248, 249, 283, 286, 287, 316.6, 913; 15/118

[56] References Cited

U.S. PATENT DOCUMENTS

Re. 27,444  7/1972  Will ....................................... 521/64
3,734,867  5/1973  Will ....................................... 521/64

FOREIGN PATENT DOCUMENTS 60138    9/1982   European Pat. Off. .
66463   12/1982   European Pat. Off. .
67016   12/1982   European Pat. Off. .
68830    1/1983   European Pat. Off. .
952075   3/1964   United Kingdom .
1458203 12/1976   United Kingdom .

*Primary Examiner*—William J. Van Balen
*Attorney, Agent, or Firm*—Milton L. Honig; James J. Farrell

[57] ABSTRACT

A highly porous polymeric material which may be dry or contain an included liquid, for example, a cleaning composition, is reinforced and rendered heat-sealable by the incorporation of thermoplastic fibrous, particulate or foraminous material. The polymeric material is preferably a styrene homo- or copolymer prepared by polymerization of a high-internal-phase emulsion. Sheets of the porous polymer may be sandwiched between two liquid-permeable substrate layers to form a wiping cloth or the like.

24 Claims, No Drawings

POROUS POLYMERIC MATERIAL CONTAINING A REINFORCING AND HEAT-SEALABLE MATERIAL

The present invention relates to a highly porous polymeric material useful for absorbing and retaining liquids. The polymer, in sheet form, may usefully be incorporated in sheet-like articles suitable for wiping surfaces, for example, the surface of a household or industrial object, or the human skin, in order either to deliver a liquid active material to that surface or to pick up liquid from that surface; or for gradually releasing an active material, such as a bubble bath composition, an air-freshener or a perfume, without surface contact.

EP No. 68 830 (Unilever) discloses an article suitable for delivering or absorbing a liquid, the article comprising a substrate carrying a pressure-sensitive porous polymeric material capable of retaining at least 5 times, and preferably at least 10 times, its own weight, defined in terms of water, of liquid, and of releasing at least some of that liquid on the application thereto of hand pressure, the porous polymeric material being dry or containing an aqueous or non-aqueous liquid.

Within that generic concept are two possibilities: the porous polymeric material may be dry, to give an article useful for mopping up liquid spillages, or it may carry a liquid which can be expressed from the article by the application of hand pressure. In some cases the polymer may contain 40 times its own weight of liquid, yet feel dry to the touch.

One class of polymers that has been found highly effective in this type of article is constituted by the polymerisation products of high internal phase emulsions, in particular styrene-based polymers European Patent Application No. EP 0 060 138A discloses and claims a class of such polymers.

In the preparing sheet-like or cloth-like articles incorporating these porous polymers difficulties have been experienced owing to the fact that these polymers are not, in general, heat-sealable. Thus a sheet of liquid-carrying polymer cannot simply be sandwiched between two layers of heat-sealable nonwoven fabric or the like and the whole heat-sealed together to form a composite cloth-like article. If the edge regions only are heat-sealed together, the porous material in the middle is not located with respect to the outer layers and can move about, resulting in crumpling or even, with some polymers, cracking.

Another problem which has been encountered is that some polymers, especially those based on styrene as the sole monomer, tend to lack mechanical strength and flexibility. These polymers are especially difficult to handle in sheet form, as is required for use in sheet-like articles for wiping surfaces and similar purposes: cracking and crumbling tends to occur.

According to a proposal described in EP No. 66 463 (Unilever), individual squares of polymer or other porous material may be located in individual cells of a sandwich structure obtained by bonding together two outer layers of nonwoven fabric or the like in a grid or similar pattern. This arrangement, while having excellent feel and giving the possibility of controlled release of liquid at different rates from different cells, has the disadvantage that assembly is difficult and slow; the squares of polymer must be accurately positioned with respect to the outer layers before bonding.

According to the present invention the porous polymeric material is modified by incorporation in the polymer of reinforcing and heat-sealable material.

The present invention accordingly provides a pressure-sensitive porous polymeric material capable of retaining at least 5 times its own weight, defined in terms of water, of liquid and of releasing at least some of that water on the application thereto of hand pressure, the porous polymeric material being dry or containing an aqueous or non-aqueous liquid, and the porous polymeric material having incorporated therein a reinforcing and heat-sealable material in fibrous, particulate or foraminous form.

The reinforcing and heat-sealable material incorporated in the porous polymer simultaneously increases the mechanical strength of the polymer, and in particular its resistance to cracking and crumbling, and enables the polymer to be heat-sealed to other heat-sealable materials.

A preferred embodiment of the present invention is a sheet-like article suitable for delivering or absorbing a liquid, the article comprising first and second sheet substrates both comprising heat-sealable material and at least one being liquid-permeable, and, sandwiched between them, an intermediate sheet of porous polymeric material according to the present invention, the article being held together by heat-sealing of each of the first and second sheet substrates to the heat-sealable reinforcing material in the intermediate sheet.

Conveniently, the heat-sealing between the outer substrate layers and the reinforcing and heat-sealable material incorporated in the intermediate layer may be along a plurality of lines distributed over the area of the article, there being sufficient heat-sealing lines present to ensure that the intermediate layer is securely located with respect to the outer layers. Conveniently the heat-sealing lines may form a regular pattern which has the additional advantage of being attractive to the consumer, for example, a series of parallel lines (giving a striped effect) or a grid pattern (giving a checker-board or diamond pattern). Additionally, it will generally be necessary for the article to be closed along the edges by bonding together, preferably by heat-sealing, the edge regions of the first and second sheet substrates. In this case these sheet substrates should be slightly larger than the intermediate porous layer.

The reinforcing and heat-sealable material is preferably in fibrous form, and more preferably in the form of a web or sheet of nonwoven, woven or knitted fabric. Loose fibres may also be used, but are less effective in improving mechanical strength. A further possibility is a foraminous, for example slitted or perforated, film or sheet. A continuous sheet is not preferred since it would prevent free movement of liquid throughout the polymer.

The reinforcing and heat-sealable material is preferably a synthetic thermoplastic material. Suitable materials which are readily heat-sealable, and which can be formed into fibres having sufficient mechanical strength, include polypropylene, nylon, polyester and acrylic polymers. If desired, mixtures of thermoplastic and non-thermoplastic fibres, for example, polypropylene and viscose, may be used to obtain an optimal balance between mechanical strength and heat-sealability.

The porous polymer of the invention may be any suitable material capable of absorbing and/or retaining the requisite amount of liquid and of releasing at least some of that liquid on the application of hand pressure.

A polymer capable of retaining at least 10 times, preferably at least 25 times and more preferably at least 40 times, its own weight of liquid, is especially advantageous. The liquid preferably constitutes at least 90%, more preferably at least 95%, of the weight of the polymer and liquid together. Details of suitable polymers are given in EP No. 68 830 (Unilever).

Such a polymer has the advantage that liquid contained in it remains enclosed within the polymer unless expressed by the application of hand pressure; the liquid-containing polymer can consist of liquid to an extent of 98% by weight or more while feeling virtually dry to the touch.

The polymer preferably has a pore volume greater than 9 cc/g, more preferably greater than 15 cc/g.

The dry density of the polymer is preferably less than 0.1 g/cc, more preferably within the range of from 0.03 to 0.08 g/cc. This is the density of the material when its pore system contains air. Some polymers according to the invention, however, cannot exist in the dry state; they are prepared by methods which leave the pore system full of liquid, and this liquid can if desired be exchanged for another liquid, but if dried their pore system collapses. Such polymers are also within the scope of the invention.

As previously indicated, in a preferred embodiment of the invention, the polymer is the polymerisation product of a high internal phase emulsion having an aqueous internal phase, and a continuous phase comprising one or more polymerisable hydrophobic monomers. It is especially preferred that the aqueous internal phase constitutes 90% or more by weight, preferably at least 95% by weight, of the emulsion. Polymers of this type are described in more detail in EP No. 60 138 and EP No. 68 830 (Unilever). If a single monomer is used, it must be hydrophobic; a monomer mixture must be predominantly hydrophobic. Vinyl polymers are of especial interest, styrene homo- and copolymers being especially preferred. Light cross-linking is of advantage in improving both the capacity for absorption and retention of liquids and the dimensional stability. Two types of polymers that have been found useful are polystyrenes lightly cross-linked with divinyl benzene, and styrene/butyl methacrylate copolymers lightly cross-linked with divinyl benzene or allyl methacrylate.

The starting emulsion preferably contains from 5 to 30% by weight of emulsifier (surfactant) and from 0.0005 to 10% by weight of a catalyst, both percentages being based on the monomers.

In this embodiment of the invention, the reinforcing and heat-sealable material is preferably incorporated in the starting emulsion and polymerisation takes place around that material. It is accordingly necessary that the material be compatible with the emulsion. More specifically, this means that the material must be hydrophobic and substantially free of water-soluble components. If the material is not intrinsically hydrophobic it may be surface-treated, for example, with a silicone polymer.

Depending on its intended use, the porous polymeric material of the invention may either be dry, i.e. contain air in its pore system, or contain a liquid. The dry polymer is useful for absorbing liquids, and may usefully be incorporated in a wiping cloth or sponge-like article for mopping up liquid spillages.

The material in its liquid-carrying form is highly useful as a carrier and controlled delivery medium for any liquid that can usefully and beneficially be delivered to a surface or other environment. Such liquids may be hydrophobic or hydrophilic; examples include soap and detergent compositions, bleach, disinfectant, bubble bath and shower preparations, air fresheners, skin treatment agents, dry cleaning solvents, perfumes, and many more.

As previously indicated, one highly useful embodiment of the invention is a sheet-like or cloth-like article in which the porous polymer is sandwiched between substrate layers. Such an article is suitable for use as a wiping cloth or for related uses not involving actual wiping, for example, delivering bath foam.

The two substrate layers may be of any suitable flexible sheet material, and may be of the same or of different materials, provided that both are heat-sealable and at least one is permeable to liquid. It is clearly essential that liquid be able to pass into and/or out of the porous polymeric core material.

Advantageously one or both substrate layers comprise paper or nonwoven fabric. The required heat-sealability may be derived from the presence of a proportion of thermoplastic fibres, or from a surface coating of thermoplastic material. In the latter case, the coating must be perforated, or sufficiently discontinuous, to allow liquid to pass through. In the finished article, the coated side will of course be innermost.

A type of material that may if desired be used for both first and second substrate layers is a porous, bulky, lofty paper or nonwoven fabric of high void volume, coated on the inner side with polyethylene film pinholed at suitable intervals.

The use of relatively absorbent material for the substrate layers is of particular advantage for an article of the invention to be used for wiping a surface in order, for example, to clean, polish, disinfect, or medically or cosmetically treat, that surface.

The article can remain dry during handling and storage, until the liquid in the polymer is released at the point of use by the application of pressure. Alternatively, the article may be wet, for example, impregnated, either with the liquid contained in the polymer or with a different liquid. If a second liquid is present, this may not necessarily be compatible with the first, since mixing will not occur until the polymer is squeezed in use. One or more further liquids may if desired be present in microencapsulated form. This is especially advantageous in the case of mutually incompatible liquids.

In one particular embodiment of the invention, a sheet-like article incorporating the polymeric material of the invention is intended for application to reflective household surfaces such as mirrors, windows, tiles, paintwork and furniture to give a substantially streak-free finish. Such an article has the advantage that it can be applied directly to the surface to be cleaned; the surface need only wiped over and then allowed to dry. No additional liquid and no cloths or tissues are required; thus contamination by streak-forming impurities is eliminated.

In this embodiment the liquid in the void system of the porous polymer is a homogeneous aqueous liquid composition having a surface tension of less than 45 mNm$^{-1}$, preferably less than 35 mNm$^{-1}$, which composition, when applied to a surface and allowed to dry, dries substantially without forming discrete droplets or particles larger than 0.25 μm, preferably 0.1 μm. The liquid preferably contains a surface-active agent, more preferably a nonionic surface-active agent, at a relatively low concentration, and a lower aliphatic alcohol, preferably ethanol or isopropanol; a film forming polymer may also be present. Suitable liquid compositions are described in detail in EP No. 67 016 and EP No. 68 830 (Unilever).

A sheet-like article containing the polymeric material of the invention may, however, be used for many other purposes, for example, hand and face cleaning; skin treatment other than cleaning (for example anti-acne treatment); baby hygiene; cleaning, polishing, disinfecting or deodorising industrial and domestic surfaces (for example, windows, paintwork, machinery, carpets, clothing, shoes); air freshening and perfume delivery; and hospital hygiene. Other possible uses will readily suggest themselves to the worker skilled in the art. The article feels to the hand like a fairly bulky cleaning cloth such as a chamois leather. In use, it is squeezed to express a suitable amount of liquid from the porous polymer.

The following Examples illustrate the invention.

EXAMPLES

Examples 1-5

Water-filled polystyrene lightly crosslinked with divinyl benzene was prepared containing various reinforcing materials, and its mechanical properties and heat-sealability were compared with those of an unreinforced polymer.

A high-internal-phase emulsion (approximately 50 ml) was prepared by mixing together the following ingredients and stirring at 300 rev/min:

| | |
|---|---|
| Styrene | 10 parts by volume |
| Divinyl benzene | 1 parts by volume |
| Double deionised water | 300 parts by weight |
| Emulsifying agent | 2 parts by weight |
| Polymerisation initiator | 0.6 parts by weight |

The emulsifying agent was sorbitan monooleate (Span (Trade Mark) 80) and the initiator was potassium persulphate.

Polymerisation was carried out in such a way as to yield thin sheets of polymer, 20 cm×20 cm×0.15 cm. Two glass plates were rendered superficially hydrophobic, and a 0.15 cm thick strip of neoprene rubber was stuck around the edge of one plate to define a square cavity 20 cm×20 cm. The cavity was filled with the emulsion, with or without reinforcing material as detailed below, the second plate was placed upon the first, and the two plates clipped together. The assembly was placed in an oven at 50° C. for 24 hours. The polymerised material could easily be removed as a sheet and cut into smaller pieces using a scalpel and straight-edge.

Where the reinforcing material was in the form of loose fibres or granules (Example 5 and comparative Example B) the fibres or granules were stirred into the emulsion before polymerisation.

Where the reinforcing material was in the form of a web, sheet or mesh (Examples 1 to 4), about half the emulsion (approximately 25 ml) was poured into the cavity on the lower plate, the web, sheet or mesh was placed on top, and the remaining emulsion poured over it, so that after polymerisation a sandwich-like structure would result.

The samples of polymer were tested for heat-sealability using a specially adapted soldering iron having an operating temperature of approximately 230° C.: the point of the soldering iron had been modified by connecting to it a 1.5 cm metal disc that was free to rotate.

A piece of polymer (6.5–13 cm$^2$) was placed between two substrates each consisting of lofty porous wet-strength paper coated with polyethylene on the side adjacent the polymer. The soldering iron was rolled in a straight line across the upper substrate while pressing downwards. This resulted in the polymer being cut through. The degree of heat-sealing that had taken place between the reinforcing material and the polyethylene coatings of the substrates was assessed by visual inspection.

The samples were also tested for mechanical strength. Each sample was placed inside an absorbent paper towel, and pressed with a flat spatula to remove most of the included water. Its resistance to being pulled apart and crumbled with the fingers was then assessed subjectively.

The results are shown in Table 1. The reinforcing materials used were as follows:

Comparative Example A: None

Example 1: a thermally bonded nonwoven fabric consisting of 50% polypropylene fibres and 50% viscose fibres, of base weight 15 g/m$^2$ (Novelin (Trade Mark) S15 ex Suominen).

Example 2: a thermally bonded nonwoven fabric consisting of 50% polypropylene fibres and 50% viscose fibres, of base weight 16 g/m$^2$ (Paratherm (Trade Mark) PS 315/16 ex Lohman).

Example 3: a polypropylene web prepared by delaminating a nonwoven fabric (Viledon (Trade Mark) T.1521).

Example 4: a mesh (polyethylene with a small percentage of polystyrene) prepared by embossing and stretching a sheet (XS 605 ex Smith & Nephew Plastics).

Example 5: loose polypropylene fibres, of average length approximately 1 cm.

TABLE 1

| Example | Wt. of reinforcement per 75 g of polymer (g) | Ratio of reinforcement to monomer (% w/v) | Mechanical strength | Heat-sealing |
|---|---|---|---|---|
| A | — | — | Poor | None (polymer cut through, polyethylene coatings of substrate bonded together) |
| 1 | 0.5 | 20 | Good | Good |
| 2 | 0.5 | 20 | Good | Very good |
| 3 | 0.5 | 20 | Good | Poor |
| 4 | 1.0 | 40 | Good | Excellent |
| 5 | 0.5 | 20 | Fairly poor | Excellent |

Examples 6-13

A similar exercise was carried out using a water-filled copolymer of styrene and butyl methacrylate. The preparation of the polymer was carried out as in Examples 1 to 5, but using a monomer mixture consisting of 7 parts by weight of styrene and 3 parts by weight of butyl methacrylate.

The results are shown in Table 2. The reinforcing materials used were as follows:

Comparative Example B: None

Example 6: polypropylene/viscose nonwoven fabric, as in Example 1.

Example 7: polypropylene/viscose nonwoven fabric, as in Example 2.
Example 8: polypropylene web, as in Example 3.
Example 9: polyethylene mesh, as in Example 4.
Example 10: a spun-bonded nonwoven fabric, 100% polypropylene, 10 g/m² (Bondina (Trade Mark) LS 5010).
Example 11: an acrylic-bonded nonwoven fabric (30% polyester, 50% nylon, 20% acrylic), 130 g/m² (Bondina (Trade Mark) Vilene (Trade Mark) 380).
Example 12: A thermally bonded nonwoven fabric (100% polyester), 97 g/m² (Cambrelle (Trade Mark) ABS ex ICI).
Example 13: loose polypropylene fibres, as in Example 5.
Comparative Example C: polyethylene granules.

TABLE 2

| Example | Wt. of reinforcement per 75 g of polymer (g) | Ratio of reinforcement to monomer (% w/v) | Mechanical strength | Heat-sealing |
|---|---|---|---|---|
| B | — | — | Poor | None (cf comparative Example A) |
| 6 | 0.5 | 20 | Good | Good |
| 7 | 0.5 | 20 | Good | Very good |
| 8 | 0.5 | 20 | Good | Poor |
| 9 | 0.5 | 20 | Good | Excellent |
| 10 | 1.0 | 40 | Good | Good |
| 11 | 0.5 | 20 | Good | Good |
| 12 | 0.5 | 20 | Good | Good |
| 13 | 0.5 | 20 | Fairly poor | Excellent |
| C | 0.75 | 30 | Poor | None (cf Comparative Example A) |

EXAMPLE 14

A more accurate comparison of mechanical strengths was carried out using an INSTRON (Trade Mark) 1122 tester, using the method set out in its instruction manual. The polypropylene web-reinforced materials of Examples 3 and 8 were compared with the corresponding unreinforced polymers of comparative Examples A and B. The results are shown in Table 3, and give an objective demonstration of the improvement in mechanical properties achieved by reinforcement in accordance with the invention.

TABLE 3

| Material | | | Work of | Ultimate |
|---|---|---|---|---|
| Reinforced | Not Reinforced | Wet or dry | fracture J m⁻² | tensile strain |
| 3 | A | dry | 18.7 | 0.015 |
|   |   | dry | 650.0 | 0.30 |
| 3 | A | wet | 415.0 | 0.10 |
|   |   | wet | 602.0 | 0.56 |
| 8 | B | dry | 275.0 | 0.11 |
|   |   | dry | 742.0 | 0.32 |

I claim:

1. A pressure-sensitive porous polymeric material capable of retaining at least 5 times its own weight, defined in terms of water, of liquid and of releasing at least some of that water on the application thereto of hand pressure, the porous polymeric material being dry or containing an aqueous or non-aqueous liquid, and the porous polymeric material having incorporated therein a reinforcing and heat-sealable material in fibrous, particulate or foraminous form.

2. The material of claim 1, wherein the reinforcing and heat-sealable material is in the form of a web or sheet of nonwoven fabric formed at least partially of thermoplastic fibres.

3. The material of claim 1, wherein the reinforcing and heat-sealable material is in the form of a mesh formed at least partially of thermoplastic sheet material.

4. The material of claim 1, wherein the reinforcing and heat-sealable material is in the form of loose fibres of thermoplastic material.

5. The material of claim 1, wherein the reinforcing and heat-sealable material comprises one or more thermoplastic materials selected from the group consisting of polypropylene, polyester, nylon and acrylic polymers.

6. The material of claim 1, which is capable of retaining at least 15 times its own weight of liquid, defined in terms of water.

7. The material of claim 6, which is capable of retaining at least 25 times its own weight of liquid, defined in terms of water.

8. The material of claim 7, which is capable of retaining at least 40 times its own weight of liquid, defined in terms of water.

9. The material of claim 1, having a dry density of less than 0.1 g/cc.

10. The material of claim 1, having a dry density within the range of from 0.03 to 0.08 g/cc.

11. The material of claim 1, comprising a cross-linked porous structure having a pore volume of more than 9 cc/g.

12. The material of claim 11, having a pore volume of more than 15 cc/g.

13. The material of claim 1, which is a homogeneous crosslinked block material.

14. The material of claim 1, which is the polymerisation product of a high internal phase emulsion having an aqueous internal phase.

15. The material of claim 14, which is the polymerisation product of a high internal phase emulsion having an aqueous internal phase which constitutes at least 90% by weight of the emulsion.

16. The material of claim 14, which is the polymerisation product of a high internal phase emulsion having an aqueous internal phase which constitutes at least 95% by weight of the emulsion.

17. A material as claimed in claim 1, which is a styrene homo- or copolymer.

18. The material of claim 17, which is a polystyrene lightly cross-linked with divinyl benzene.

19. The material of claim 17, which is a styrene/butyl methacrylate copolymer lightly cross-linked with divinyl benzene or allyl methacrylate.

20. A sheet-like article suitable for delivering or absorbing a liquid, the article comprising first and second sheet substrates both comprising heat-sealable material and at least one being liquid-permeable, and, sandwiched between them, an intermediate sheet of the reinforced porous polymeric material of claim 1, the first and second sheet substrates each being heat-sealed to the reinforcing and heat-sealable material in the intermediate sheet.

21. The article of claim 20, wherein the heat-sealing is in the form of a plurality of lines distributed over the area of the article.

22. The article of claim 20, wherein one or both of the first and second substrate layers comprises paper or nonwoven fabric.

23. The article of claim 22, wherein one or both of the first and second substrate layers comprises paper or nonwoven fabric having a coating of thermoplastic film, said coating being provided with pinholes for the passage of liquid.

24. The article of claim 20, wherein the porous polymeric material of the intermediate layer contains a homogeneous aqueous liquid composition having a surface tension of less than 45 mNm$^{-1}$, which composition, when applied to a surface and allowed to dry, dries substantially without forming discrete droplets or particles larger than 0.25 μm.

* * * * *